United States Patent
Hebert et al.

(10) Patent No.: US 9,114,038 B2
(45) Date of Patent: *Aug. 25, 2015

(54) METHOD OF DELIVERING A STENT

(75) Inventors: Stephen Hebert, San Francisco, CA (US); Marc-Alan Levine, Pottstown, PA (US)

(73) Assignee: BACK BAY MEDICAL INC., Costa Mesa, CA (US)

(*) Notice: Subject to any disclaimer, the term of this patent is extended or adjusted under 35 U.S.C. 154(b) by 259 days.

This patent is subject to a terminal disclaimer.

(21) Appl. No.: 11/897,821

(22) Filed: Aug. 31, 2007

(65) Prior Publication Data
US 2007/0299502 A1  Dec. 27, 2007

Related U.S. Application Data

(63) Continuation of application No. 11/248,362, filed on Oct. 11, 2005, now abandoned, which is a continuation of application No. 10/087,127, filed on Feb. 28, 2002, now Pat. No. 6,989,024.

(51) Int. Cl.
*A61F 2/966* (2013.01)
*A61F 2/95* (2013.01)
(Continued)

(52) U.S. Cl.
CPC . *A61F 2/966* (2013.01); *A61F 2/95* (2013.01); *A61F 2/958* (2013.01); *A61M 25/09* (2013.01); *A61F 2002/9583* (2013.01); *A61M 2025/09008* (2013.01); *A61M 2025/09183* (2013.01)

(58) Field of Classification Search
CPC ..... A61B 17/12118; A61F 2/95; A61F 2/958; A61F 2/966; A61F 2/91
USPC ............. 623/1.11, 1.12, 1.23, 1.15; 606/108, 606/191, 194, 198, 200; 600/585
See application file for complete search history.

(56) References Cited

U.S. PATENT DOCUMENTS 3,485,234 A   12/1969 Stevens
3,517,128 A    6/1970 Hines
(Continued)

FOREIGN PATENT DOCUMENTS

EP   0686379 B2   12/1995
EP   0696447 B1    2/1996
(Continued)

OTHER PUBLICATIONS

Abbott Vascular. "Hi-Torque Standard Guide Wire." Jan. 31, 2001. <www.abbotvascular.com/us/hi-torque-standard.html>.*
(Continued)

*Primary Examiner* — Katherine M Shi
(74) *Attorney, Agent, or Firm* — Peter B. Scull; Hamilton, DeSanctis & Cha LLP

(57) ABSTRACT

A guidewire loaded stent for delivery through a catheter is described herein. The stent delivery assembly can deliver and place a stent within tortuous regions of the body which are accessible to guidewires but inaccessible to stenting catheters. The assembly comprises a guidewire covered in part by a retractable sheath and a radially expandable stent near or at the distal end of the guidewire. The whole assembly is advanced through conventional catheters or it may be used alone. In either case, when the stent is adjacent to a treatment site within the body, the sheath is retracted proximally to expose the stent for radial expansion into contact with the vessel wall. Radio-opaque marker bands are optionally located on either side or both sides of the stent on the guidewire body to aid in visual placement. The assembly can optionally include an expandable balloon on the guidewire for different treatment modalities.

2 Claims, 6 Drawing Sheets

(51) Int. Cl.
    *A61F 2/958*    (2013.01)
    *A61M 25/09*    (2006.01)

(56) References Cited

U.S. PATENT DOCUMENTS

| | | |
|---|---|---|
| 4,586,923 A | 5/1986 | Gould |
| 4,665,918 A | 5/1987 | Garza |
| 4,768,507 A | 9/1988 | Fischell |
| 4,787,884 A | 11/1988 | Goldberg |
| 4,969,890 A | 11/1990 | Sugita |
| 4,990,151 A | 2/1991 | Wallsten |
| 4,994,071 A | 2/1991 | MacGregor |
| 5,034,001 A | 7/1991 | Garrison |
| 5,089,005 A | 2/1992 | Harada |
| 5,092,877 A | 3/1992 | Pinchuk |
| 5,098,440 A | 3/1992 | Hillstead |
| 5,147,370 A | 9/1992 | McNamara |
| 5,342,387 A | 8/1994 | Summers |
| 5,368,592 A | 11/1994 | Stern |
| 5,391,146 A | 2/1995 | That |
| 5,453,090 A | 9/1995 | Martinez |
| 5,458,615 A | 10/1995 | Klemn |
| 5,464,408 A | 11/1995 | Duc |
| 5,484,444 A | 1/1996 | Braunschweiler |
| 5,498,227 A | 3/1996 | Mawad |
| 5,534,007 A | 7/1996 | St. Germain |
| 5,571,086 A | 11/1996 | Kaplan |
| 5,571,135 A | 11/1996 | Fraser |
| 5,607,466 A | 3/1997 | Imbert |
| 5,669,880 A * | 9/1997 | Solar ............... 623/1.11 |
| 5,669,924 A | 9/1997 | Shaknovich |
| 5,683,451 A | 11/1997 | Lenker |
| 5,693,083 A | 12/1997 | Baker et al. |
| 5,695,499 A | 12/1997 | Helgerson et al. |
| 5,702,418 A | 12/1997 | Ravenscroft |
| 5,735,859 A | 4/1998 | Fischell |
| 5,749,825 A | 5/1998 | Fischell |
| 5,755,708 A | 5/1998 | Segal |
| 5,772,669 A | 6/1998 | Vrba |
| 5,776,141 A | 7/1998 | Klein |
| 5,782,855 A | 7/1998 | Lau |
| 5,788,707 A | 8/1998 | Del Toro |
| 5,797,952 A | 8/1998 | Klein |
| 5,807,398 A | 9/1998 | Shaknovich |
| 5,824,041 A | 10/1998 | Lenker |
| 5,824,055 A | 10/1998 | Spiridigliozzi |
| 5,843,090 A | 12/1998 | Schuetz |
| 5,846,210 A | 12/1998 | Ogawa et al. |
| 5,906,640 A | 5/1999 | Penn |
| 5,910,144 A | 6/1999 | Hayashi |
| 5,957,929 A | 9/1999 | Brenneman |
| 5,961,548 A | 10/1999 | Shmulewitz |
| 5,980,514 A | 11/1999 | Kupiecki et al. |
| 5,980,533 A | 11/1999 | Holman |
| 5,984,929 A | 11/1999 | Bashiri et al. |
| 5,989,263 A * | 11/1999 | Shmulewitz ............... 606/108 |
| 5,989,280 A | 11/1999 | Euteneuer |
| 6,007,573 A * | 12/1999 | Wallace et al. ............... 623/1.11 |
| 6,024,763 A | 2/2000 | Lenker et al. |
| 6,042,588 A | 3/2000 | Munsinger |
| 6,056,775 A | 5/2000 | Borghi |
| 6,063,111 A | 5/2000 | Hieshima et al. |
| 6,071,286 A | 6/2000 | Mawad |
| 6,102,918 A | 8/2000 | Kerr |
| 6,120,533 A * | 9/2000 | Fischell ............... 623/1.11 |
| 6,126,685 A | 10/2000 | Lenker et al. |
| 6,146,415 A | 11/2000 | Fitz |
| 6,156,063 A | 12/2000 | Douglas |
| 6,168,579 B1 | 1/2001 | Tsugita |
| 6,168,617 B1 | 1/2001 | Blaeser |
| 6,171,328 B1 | 1/2001 | Addis |
| 6,179,859 B1 | 1/2001 | Bates |
| 6,183,481 B1 | 2/2001 | Lee |
| 6,187,015 B1 | 2/2001 | Brenneman |
| 6,187,016 B1 | 2/2001 | Hedges |
| 6,190,402 B1 * | 2/2001 | Horton et al. ............... 623/1.11 |
| 6,210,429 B1 | 4/2001 | Vardi |
| 6,214,036 B1 | 4/2001 | Letendre et al. |
| 6,217,585 B1 | 4/2001 | Houser |
| 6,241,758 B1 | 6/2001 | Cox |
| 6,245,045 B1 | 6/2001 | Stratienko |
| 6,254,609 B1 | 7/2001 | Vrba |
| 6,254,628 B1 | 7/2001 | Wallace |
| 6,264,671 B1 | 7/2001 | Stack |
| 6,264,682 B1 | 7/2001 | Wilson |
| 6,270,521 B1 | 8/2001 | Fischell |
| 6,280,465 B1 | 8/2001 | Cryer |
| 6,287,331 B1 * | 9/2001 | Heath ............... 623/1.15 |
| 6,296,622 B1 | 10/2001 | Kurz |
| 6,322,586 B1 | 11/2001 | Monroe |
| 6,350,278 B1 | 2/2002 | Lenker |
| 6,355,060 B1 | 3/2002 | Lenker et al. |
| 6,368,344 B1 | 4/2002 | Fitz |
| 6,390,993 B1 | 5/2002 | Cornish |
| 6,391,044 B1 | 5/2002 | Yadav |
| 6,391,050 B1 | 5/2002 | Broome |
| 6,391,051 B2 | 5/2002 | Sullivan, III |
| 6,409,750 B1 | 6/2002 | Hyodoh |
| 6,425,898 B1 * | 7/2002 | Wilson et al. ............... 606/108 |
| 6,468,298 B1 | 10/2002 | Pelton |
| 6,508,825 B1 | 1/2003 | Selmon |
| 6,514,280 B1 | 2/2003 | Gilson |
| 6,514,281 B1 | 2/2003 | Blaeser |
| 6,520,988 B1 | 2/2003 | Colombo |
| 6,562,064 B1 | 5/2003 | DeBeer |
| 6,582,460 B1 | 6/2003 | Cryer |
| 6,592,549 B2 | 7/2003 | Gerdts |
| 6,607,551 B1 | 8/2003 | Sullivan |
| 6,626,934 B2 | 9/2003 | Blaeser |
| 6,673,025 B1 | 1/2004 | Richardson |
| 6,679,909 B2 | 1/2004 | McIntosh |
| 6,695,862 B2 | 2/2004 | Cox |
| 6,716,238 B2 | 4/2004 | Elliott |
| 6,743,219 B1 | 6/2004 | Dwyer |
| 6,755,846 B1 | 6/2004 | Yadav |
| 6,802,846 B2 | 10/2004 | Hauschild |
| 6,833,003 B2 | 12/2004 | Jones |
| 6,840,950 B2 | 1/2005 | Stanford |
| 6,860,898 B2 | 3/2005 | Stack |
| 6,890,349 B2 | 5/2005 | McGuckin, Jr. |
| 6,908,477 B2 | 6/2005 | McGuckin, Jr. |
| 6,926,732 B2 | 8/2005 | Derus |
| 6,932,836 B2 | 8/2005 | Amin |
| 6,936,065 B2 | 8/2005 | Khan |
| 6,939,368 B2 | 9/2005 | Simso |
| 6,945,989 B1 | 9/2005 | Betelia |
| 6,955,685 B2 | 10/2005 | Escamilla |
| 6,960,227 B2 | 11/2005 | Jones |
| 6,989,024 B2 | 1/2006 | Hebert |
| 7,001,422 B2 | 2/2006 | Escamilla |
| 7,004,964 B2 | 2/2006 | Thompson |
| 7,011,673 B2 | 3/2006 | Fischell |
| 7,037,330 B1 | 5/2006 | Rivelli, Jr. |
| 7,063,719 B2 | 6/2006 | Jansen |
| 7,182,779 B2 | 2/2007 | Acosta |
| 7,195,648 B2 | 3/2007 | Jones et al. |
| 7,201,769 B2 | 4/2007 | Jones et al. |
| 2001/0003801 A1 | 6/2001 | Strecker |
| 2001/0027323 A1 | 10/2001 | Sullivan, III |
| 2001/0037126 A1 | 11/2001 | Stack |
| 2002/0049487 A1 | 4/2002 | Lootz |
| 2002/0087046 A1 * | 7/2002 | Sullivan et al. ............... 600/36 |
| 2002/0091436 A1 * | 7/2002 | Phelps et al. ............... 623/1.11 |
| 2002/0120323 A1 | 8/2002 | Thompson et al. |
| 2002/0161427 A1 | 10/2002 | Rabkin |
| 2003/0199965 A1 | 10/2003 | Jansen et al. |
| 2003/0208222 A1 | 11/2003 | Zadno-Azizi |
| 2003/0216807 A1 | 11/2003 | Jones et al. |
| 2004/0010265 A1 | 1/2004 | Karpiel |
| 2004/0059407 A1 | 3/2004 | Escamilla |
| 2004/0193178 A1 | 9/2004 | Nikolchev |
| 2004/0193179 A1 | 9/2004 | Nikolchev |
| 2004/0220585 A1 | 11/2004 | Nikolchev |
| 2004/0260381 A1 | 12/2004 | Marco |

(56) References Cited

U.S. PATENT DOCUMENTS

| | | |
|---|---|---|
| 2004/0260385 A1 | 12/2004 | Jones |
| 2005/0038496 A1 | 2/2005 | Jones et al. |
| 2005/0049666 A1 | 3/2005 | Chien et al. |
| 2005/0209670 A1 | 9/2005 | George |
| 2005/0209671 A1 | 9/2005 | Ton |
| 2005/0209672 A1 | 9/2005 | George |
| 2005/0209675 A1 | 9/2005 | Ton |
| 2005/0246008 A1 | 11/2005 | Hogendijk |
| 2006/0041302 A1 | 2/2006 | Malewicz |
| 2006/0085057 A1 | 4/2006 | George |
| 2006/0136037 A1 | 6/2006 | DeBeer |
| 2006/0149355 A1 | 7/2006 | Mitelberg et al. |
| 2006/0200221 A1 | 9/2006 | Malewicz |
| 2006/0204547 A1 | 9/2006 | Nguyen et al. |
| 2006/0206200 A1 | 9/2006 | Garcia |
| 2006/0206201 A1 | 9/2006 | Garcia |
| 2006/0271149 A1 | 11/2006 | Berez |
| 2006/0271153 A1 | 11/2006 | Garcia |
| 2007/0027522 A1 | 2/2007 | Chang |
| 2007/0043419 A1 | 2/2007 | Nikolchev |
| 2007/0043420 A1 | 2/2007 | Lostetter |
| 2007/0055339 A1 | 3/2007 | George |
| 2007/0073379 A1 | 3/2007 | Chang |
| 2008/0114442 A1 | 5/2008 | Mitchell et al. |

FOREIGN PATENT DOCUMENTS

| | | |
|---|---|---|
| EP | 0792627 B2 | 9/1997 |
| EP | 0943302 B1 | 9/1999 |
| EP | 0997116 | 5/2000 |
| EP | 1157673 | 11/2001 |
| WO | WO9639998 | 12/1996 |
| WO | WO9707756 | 3/1997 |
| WO | WO9745073 | 12/1997 |
| WO | WO9849983 | 11/1998 |
| WO | WO9934749 | 7/1999 |
| WO | WO9936002 | 7/1999 |
| WO | WO0000190 | 2/2000 |
| WO | WO0009190 | 2/2000 |
| WO | WO0009190 A1 | 2/2000 |
| WO | WO0012030 A1 | 3/2000 |
| WO | WO0072780 | 12/2000 |
| WO | WO0149214 | 7/2001 |
| WO | WO02067782 A2 | 9/2002 |
| WO | WO02067782 A3 | 9/2002 |
| WO | WO03041610 | 5/2003 |

OTHER PUBLICATIONS

Merriam-Webster dictionary definition of "wire".*
Appeal Brief filed Aug. 27, 2013 for U.S. Appl. No. 11/335,205.*
Merriam-Webster dictionary definition of "wire" accessed on Oct. 30, 2013.*
Stephen Hebert, First Preliminary Amendment., U.S. Appl. No. 10/087,127, "Guidewire Loaded Stent for Delivery through a Catheter", May 29, 2003.
USPTO., Non Final Office Action., U.S. Appl. No. 10/087,127, "Guidewire Loaded Stent for Delivery through a Catheter", May 11, 2004.
Stephen Hebert, Response to Restriction Requirement., U.S. Appl. No. 10/087,127, "Guidewire Loaded Stent for Delivery through a Catheter"., Jun. 14, 2004.
USPTO., Non Final Office Action., U.S. Appl. No. 10/087,127, "Guidewire Loaded Stent for Delivery through a Catheter", Aug. 27, 2004.
Stephen Hebert, Amendment in Response to Non Final Office Action., U.S. Appl. No. 10/087,127, "Guidewire Loaded Stent for Delivery through a Catheter", Nov. 29, 2004.
USPTO., Final Office Action., U.S. Appl. No. 10/087,127, "Guidewire Loaded Stent for Delivery through a Catheter", Feb. 7, 2005.
Stephen Hebert., Response to Final Office Action., U.S. Appl. No. 10/087,127, "Guidewire Loaded Stent for Delivery through a Catheter", Apr. 1, 2005.
USPTO., Advisory Action Before the Filing of an Appeal Brief., U.S. Appl. No. 10/087,127, "Guidewire Loaded Stent for Delivery through a Catheter", Apr. 14, 2005.
Stephen Hebert., Request for Continued Examination and Amendment., U.S. Appl. No. 10/087,127, "Guidewire Loaded Stent for Delivery through a Catheter", May 9, 2005.
USPTO., Interview Summary., U.S. Appl. No. 10/087,127, "Guidewire Loaded Stent for Delivery through a Catheter", May 11, 2005.
USPTO., Non Final Office Action., U.S. Appl. No. 10/087,127, "Guidewire Loaded Stent for Delivery through a Catheter", Jun. 10, 2005.
USPTO., Interview Summary., U.S. Appl. No. 10/087,127, "Guidewire Loaded Stent for Delivery through a Catheter", Aug. 8, 2005.
Stephen Hebert., Amendment in Response to the Office Action of Jun. 10, 2005., U.S. Appl. No. 10/087,127, "Guidewire Loaded Stent for Delivery through a Catheter", Aug. 9, 2005.
USPTO., Notice of Allowance and Fee(s) Due., U.S. Appl. No. 10/087,127, "Guidewire Loaded Stent for Delivery through a Catheter", Sep. 19, 2005.
Notification of Transmittal of the International Search Report and the Written Opinion of the International Searching Authority, or the Declaration for International Application No. PCT/US2009/046633.
European Patent Opposition Papers for EP Patent No. B1872742, Application No. 07116739.9; EPO Examination Document in preparation for Oral Proceedings; Jun. 30, 2011; European Patent Office (EPO), Berlin Germany.
European Patent Opposition Papers for EP Patent No. B1872742, Application No. 07116739.9; Letter from Opposer regarding the Opposition Procedure; Frank Peterreins, Fish & Richardson P.C., Munich Germany to the EPO, Mar. 7, 2011.
European Patent Opposition Papers for EP Patent No. B1872742, Application No. 07116739.9; Reply of the Proprieto to the Notice of the Opposition; Susanna Joyce Fish, Boult Wade Tennant, London, United Kingdom, to the EPO, Oct. 11, 2010.
European Patent Opposition Papers for EP Patent No. B1872742, Application No. 07116739.9; Communication/Notice from the EPO of Opposition to Proprietor representative, Zea, Barlocci & Markvardsen, mailed Jan. 15, 2010; including Opposition Memorandum from Opposer representative, Frank Peterreins, Fish & Richardson P.C., Munich Germany to the EPO, Jan. 8, 2010.
Supplementary European Search Report, European Application, EP03743674, Applicant: Counter Clockwise, Inc., Nov. 17, 2006, European Patent Office Rijswijk, Netherlands (place of search Berlin, Germany, completion of search Nov. 8, 2006).
Supplementary European Search Report (17.11.06).
Cordis Neurovascular, Inc., 2002 US ref: 152-7369-2; Johnson & Johnson Medical NV/SA EU ref: 2E-800-0475-4; "Rapidtransit Microcatheter 18 System through tortuous vasculature".
Randall T. Higashida, et al., "Initial Clinical Experience with a New Self-Expanding Nitinol Stent for the Treatment of Intracranial Cerebral Aneurysms: The Cordis Enterprise Stent", pp. 1751-1756, Aug. 2005.
Alexandre C. Abizaid, et al., "The CariodMind coronary stent delivery system", Europe Edition 2007, pp. 154-157.

* cited by examiner

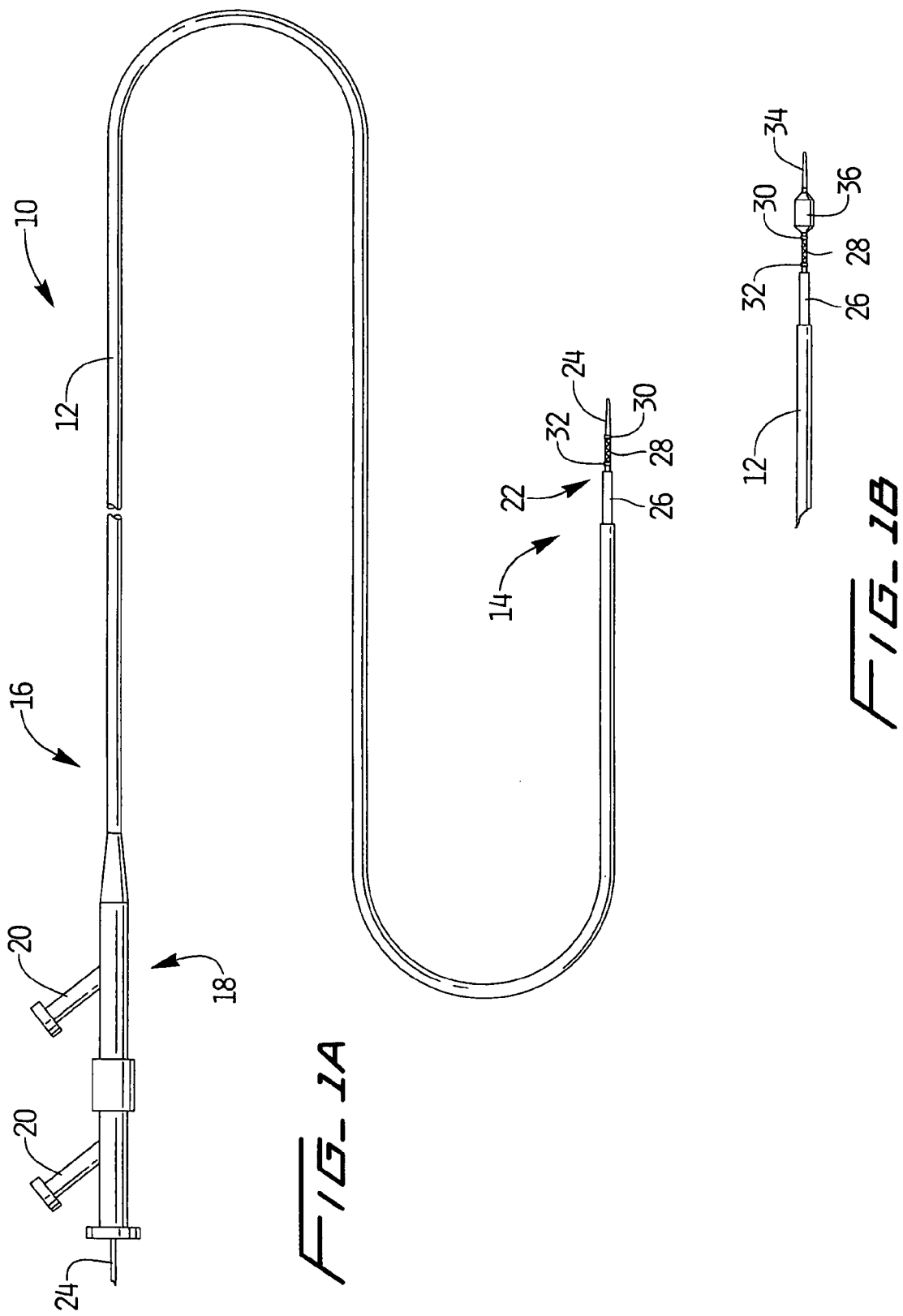

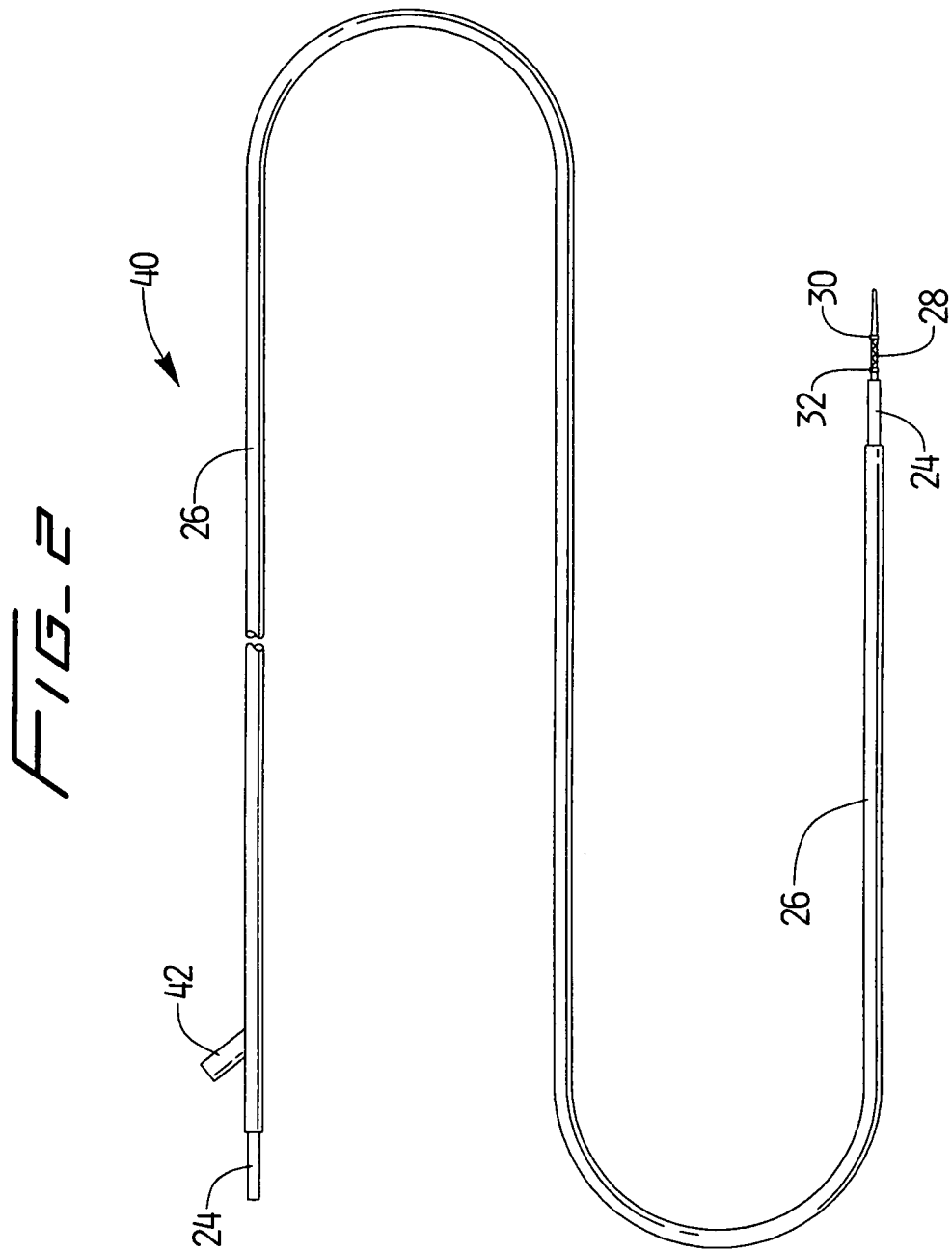

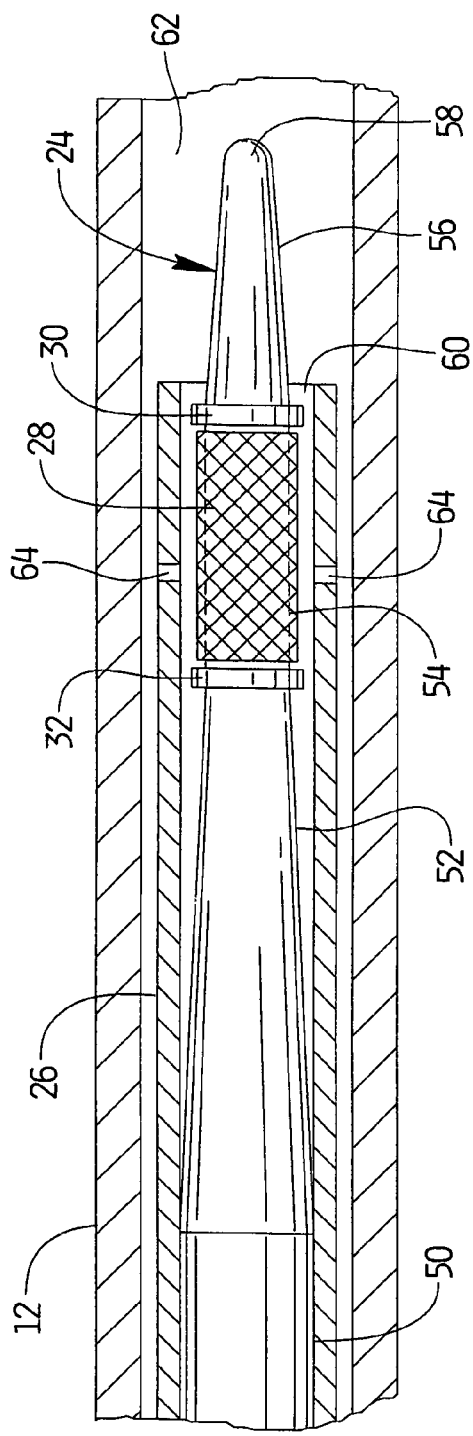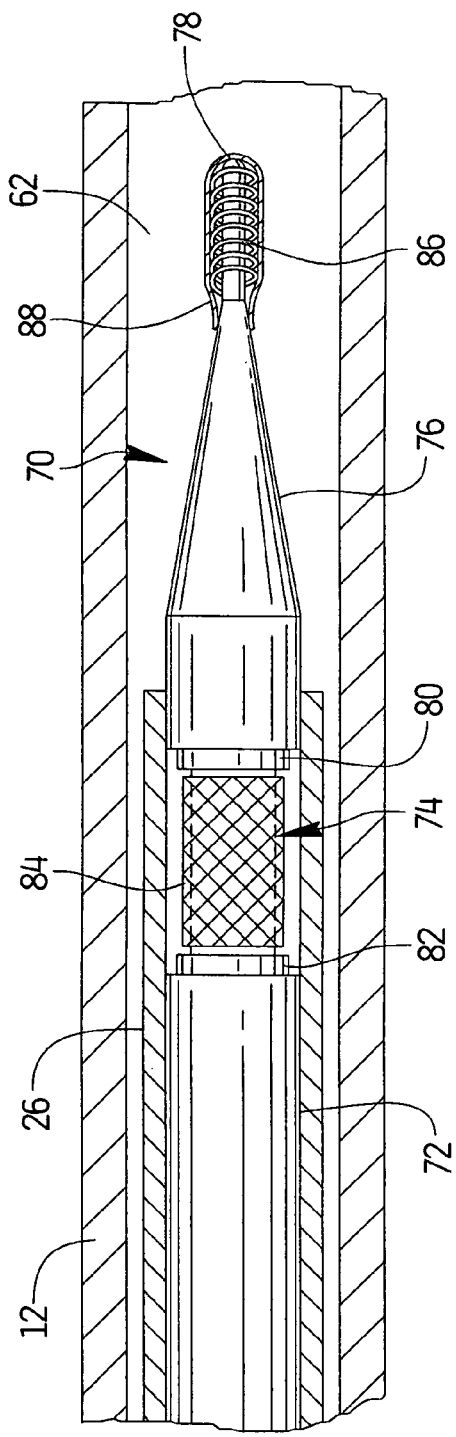

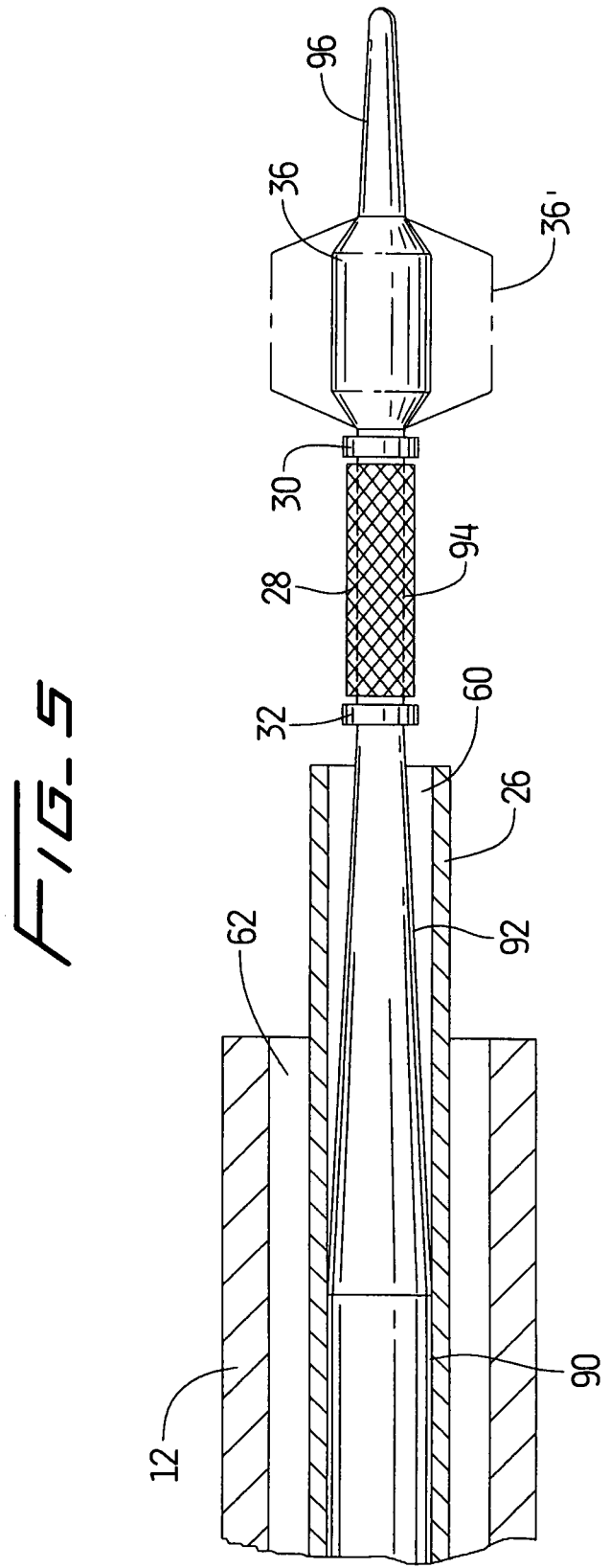

FIG_6A
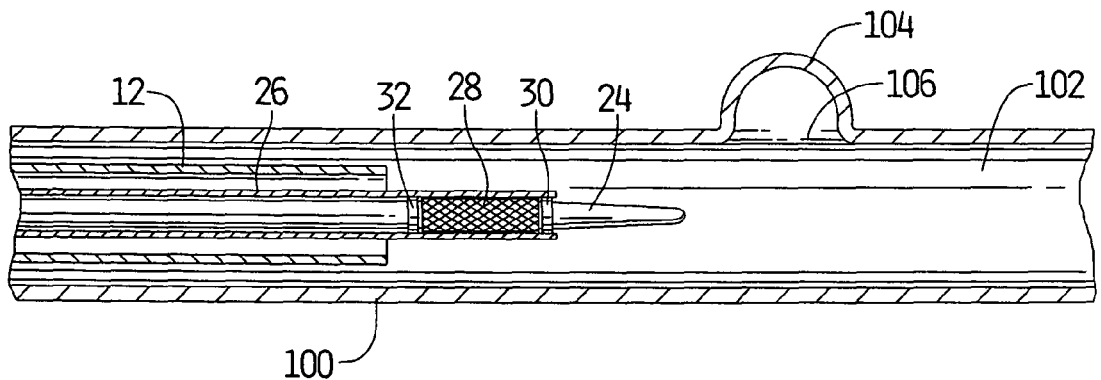
FIG_6B
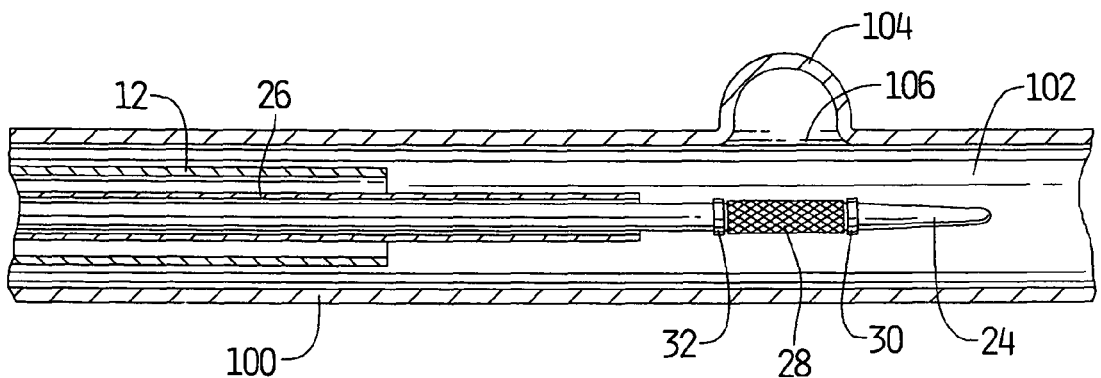
FIG_6C
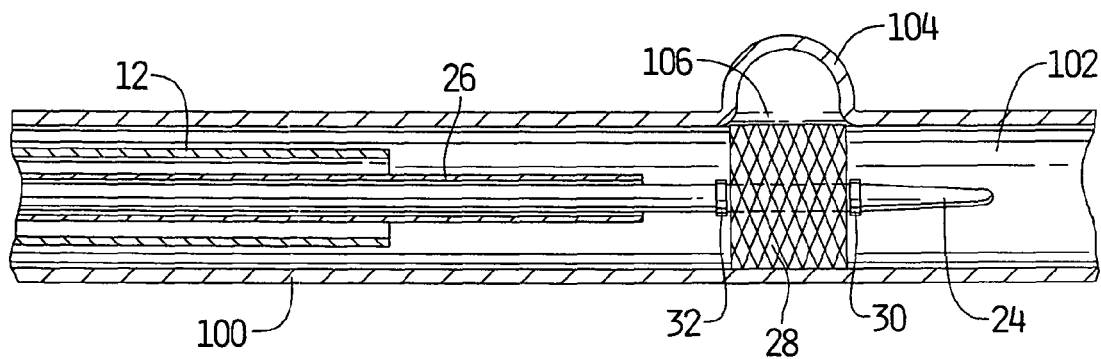

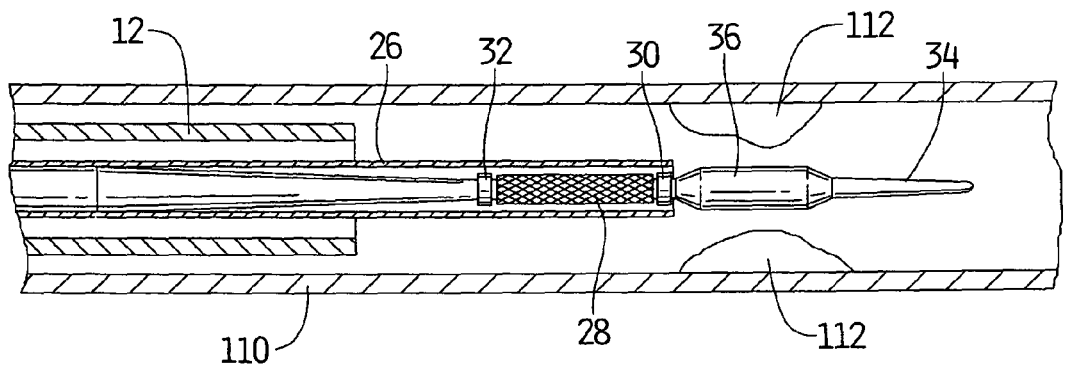
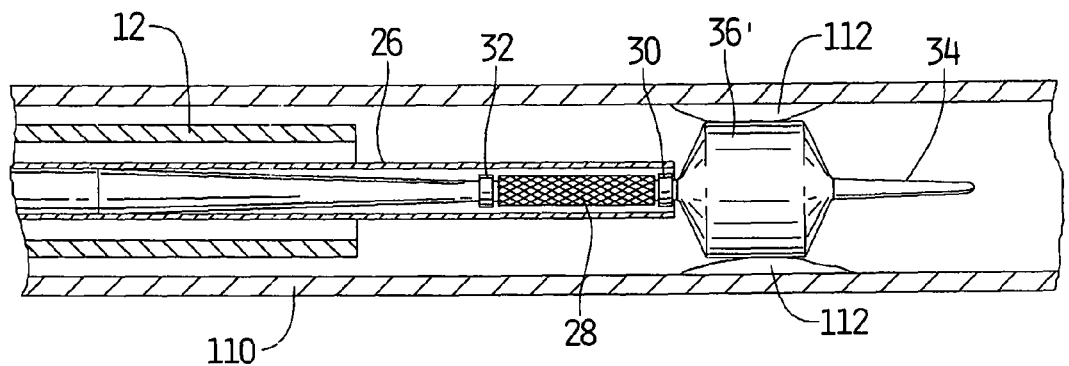
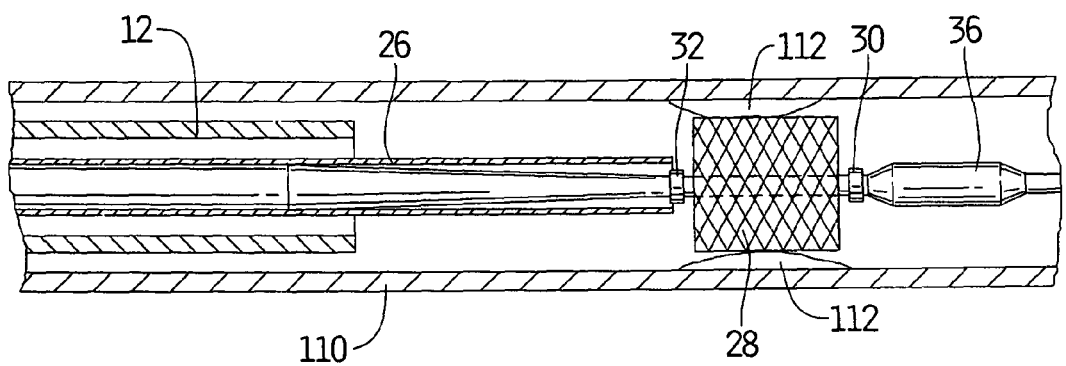

METHOD OF DELIVERING A STENT

This application is a continuation of application Ser. No. 11/248,362, filed Oct. 11, 2005 which is a continuation of application Ser. No. 10/087,127, filed Feb. 28, 2002, now U.S. Pat. No. 6,989,024, the entire contents of which are incorporated herein by reference.

TECHNICAL FIELD OF THE INVENTION

The present invention relates generally to catheters and intravascular medical procedures. More particularly, it relates to methods and apparatus for delivering a stent through a catheter by way of a guidewire delivery device.

BACKGROUND ART OF THE INVENTION

Intravascular stents are well known in the medical arts for the treatment of vascular stenoses. Stents are prostheses which are generally tubular and which expand radially in a vessel or lumen to maintain its patency. For deployment within the body's vascular system, most stents are mounted onto a balloon angioplasty catheter for deployment by balloon expansion at the site of a dilated stenosis or an aneurysm. Self-expanding stents, which typically expand from a compressed delivery position to its original diameter when released from the delivery device, generally exert a radial force on the constricted portion of the body lumen to re-establish patency. One common self-expanding stent is manufactured of Nitinol, a nickel-titanium shape memory alloy, which can be formed and annealed, deformed at a low temperature, and recalled to its original shape with heating, such as when deployed at body temperature in the body.

To position a stent across an area of stenosis or an aneurysm, a guiding catheter having a preformed distal tip is percutaneously introduced into the vascular system of a patient by way of, e.g., a conventional Seldinger technique, and advanced within the vasculature until the distal tip of the guiding catheter is seated in the ostium of a desired artery. A guidewire is then positioned within an inner lumen of a dilatation catheter and then both are advanced through the guiding catheter to the distal end thereof. The guidewire must first be advanced out of the distal end of the guiding catheter into the patient's coronary vasculature until the distal end of the guidewire crosses a lesion to be dilated, then the catheter having a stent positioned on the distal portion is advanced into the patient's vasculature over the previously introduced guidewire until the stent is properly positioned across the lesion. Once in position, the stent may be released accordingly.

It is generally desirable to have catheters which present small cross sectional diameters to enable access into small sized vessels. However, conventional techniques and apparatus typically require the use of a guidewire for the desirable placement of the catheter and stent within the vasculature. Thus, conventional catheters typically require a separate lumen within the catheter body to allow for the passage of a guidewire therethrough. This separate lumen necessarily adds to the cross sectional profile of the device. Yet vasculature having a tortuous path and/or a small diameter, such as the intracranial vasculature, present problems for the conventional stenting catheter. Accordingly, a highly flexible stenting apparatus which is capable of accessing tortuous regions and which presents a small cross section is needed.

SUMMARY OF THE INVENTION

A highly flexible stent delivery assembly is described below. The assembly has the desirable characteristics of guidewires in traversing tortuous vasculature, including small cross sectioned vessels. The stent delivery assembly of the present invention is thus able to deliver and place a stent anywhere in the vasculature or within the body that is readily accessible by a guidewire but is not normally accessible by a stenting catheter body which would ride over such a guidewire.

The stent delivery assembly may typically comprise a guidewire body which is preferably covered at least in part by a retractable sheath. A radially expandable stent is disposed directly in contact about the guidewire preferably near or at the distal end of the guidewire. The retractable sheath preferably covers the entire stent during deployment and placement, and is retractable proximally to uncover or expose the stent for radial expansion. A pair of optionally placed radio-opaque marker bands may be located on either side (distally or proximally) or both sides of the stent on the guidewire body.

The sheath may have a flush port, which is in fluid communication with the distal end of the assembly, located near the proximal end of the sheath. The flush port enables a fluid, e.g., saline, to be passed through the assembly prior to insertion into the vasculature for flushing out air or debris trapped between the sheath and guidewire. It may also be used to deliver drugs or fluids within the vasculature as desired.

Because the guidewire body, rather than a catheter body, carries and delivers the stent through the vasculature, the stent may be placed almost anywhere in the body accessible by a conventional guidewire. This may include, e.g., the tortuous intracranial vasculature as well as, e.g., the more accessible coronary vasculature. Furthermore, the assembly, which may include the guidewire, sheath, and stent, may be introduced into a wide variety of conventional catheters. This portability allows for flexibility in using the same type of assembly in an array of conventional catheters depending upon the desired application and the region of the body to be accessed.

The sheath may be made from various thermoplastics, e.g., PTFE, FEP, Tecoflex, etc., which may optionally be lined on the inner surface of the sheath or on the outer surface of the guidewire or on both with a hydrophilic material such as Tecoflex or some other plastic coating. Additionally, either surface may be coated with various combinations of different materials, depending upon the desired results. It is also preferably made to have a wall thickness of about, e.g., 0.001 in., thick and may have an outer diameter ranging from about 0.0145 to 0.016 in. or greater. The sheath may be simply placed over the guidewire and stent, or it may be heatshrinked to conform closely to the assembly.

The guidewire body may be made of a conventional guidewire or it may also be formed from a hypotube having an initial diameter ranging from 0.007 to 0.014 in. Possible materials may include superelastic metals and alloys, e.g., Nitinol, or metals such as stainless steel, or non-metallic materials, e.g., polyimide. The hypotube may be further melted or ground down, depending upon the type of material used, into several sections of differing diameters. The distal end of the guidewire may be further tapered and is preferably rounded to aid in advancement through the vasculature. Radio-opaque coils may be placed over a portion of distal end to aid in radiographic visualization.

The stent may be configured to be self expanding from a constrained first configuration when placed upon guidewire to a larger expanded second configuration when deployed. When the sheath is retracted proximally, the stent preferably self expands to a preconfigured diameter of, e.g., about 0.060 in. (1.5 mm), and up to a diameter of about 0.315 in. (8 mm).

Various materials may be used to construct the stent such as platinum, Nitinol, other shape memory alloys, or other self expanding materials.

Other variations may include a guidewire which defines a stepped section near the distal end of the guidewire. The stepped section outer diameter is less than the uniform diameter defined by the remainder of the guidewire. The stent may be placed over this section while maintaining a flush outer diameter which may facilitate delivery of the stent-guidewire assembly not only through catheter body but within the vasculature. The guidewire may be further formed into tapered section distally of the stepped section.

When in use in tortuous pathways, such as intracranial vessels, the guidewire assembly may be used with the sheath alone or in combination with a delivery catheter. The catheter body may be advanced within the vessel to a treatment location such as an aneurysm. Once the catheter is near the treatment site, the guidewire may be advanced out of the catheter and adjacent the treatment site. The sheath may then be retracted proximally to expose the stent to radially expand into contact with the walls of the vessel. Alternatively, the sheath may be held stationary while the guidewire and stent are advanced to expose the stent, e.g., as when deploying a coil stent. The stent may be self expanding or configured to expand upon the application of an electric current with or without the sheath. In either case, once the stent has been released from the guidewire and expanded, both the guidewire and sheath may be withdrawn into the catheter body and removed from the vicinity. The catheter may be left within the vessel to allow for the insertion of additional tools or the application of drugs near the treatment site.

Other variations may include an expandable balloon section preferably located distally of the stent. In this case, treatment preferably includes the expansion of the balloon first to mitigate any occlusions within the vessel. The stent may then be released in a manner similar to that described above. Once the balloon has been deflated and the stent expanded, the assembly may be removed from the vicinity.

BRIEF DESCRIPTION OF THE DRAWINGS

FIG. 1A shows a variation on the stent delivery assembly where a guidewire has a stent disposed on the wire near its distal end.

FIG. 1B shows another variation on the assembly where the guidewire may have an expandable balloon located near the distal end of the wire.

FIG. 2 shows a representative illustration of the guidewire and stent assembly which is insertable within a catheter; the assembly shows the guidewire surrounded by a partially retracted sheath which exposes the stent.

FIG. 3 shows a cross sectioned side view of a variation of the stent delivery assembly placed within a catheter body lumen.

FIG. 4 shows a cross sectioned side view of another variation of the stent delivery assembly also placed within a catheter body lumen.

FIG. 5 shows a cross sectioned side view of yet another variation of the stent delivery assembly having an expandable balloon section.

FIGS. 6A to 6C illustrate an example of one method of placing a stent within a hollow body organ using the guidewire assembly.

FIGS. 7A to 7C illustrate an example of another method of placing a stent within the hollow body organ in combination with an expandable balloon.

DETAILED DESCRIPTION OF THE INVENTION

A stent delivery assembly having a small cross section and which is highly flexible is described herein. As shown in FIG. 1A, catheter assembly 10 is comprised of a conventional catheter body 12 having a distal end 14 and a proximal end 16. A fitting assembly 18 is attached to the proximal end 16 and may preferably have various attachments, e.g., Luer lock 20, to allow for access to catheter body 12 or the use of other instruments. Conventional catheter body 12 shows guidewire assembly 22 being slidably positioned therewithin. Assembly 22, which is described in further detail below, is shown in this variation as having a guidewire body 24 preferably covered at least in part by a retractable sheath 26. A radially expandable stent 28 is preferably disposed near the distal end of guidewire 24. Stent 28 may also be placed between an optional pair of radio-opaque marker bands 30, 32. One or both marker bands 30, 32 may be used or they may be left off the assembly entirely. The use of radio-opaque material allows for the visualization of the assembly during placement within the vasculature. Such visualization techniques may include conventional methods such as fluoroscopy, radiography, ultrasonography, magnetic resonance imaging, etc.

FIG. 1B shows the distal portion of catheter body 12 with another guidewire variation 34 which has an optional angioplasty balloon 36. As shown in this variation, balloon 36 is preferably located distally of stent 28 and may be sufficiently deflated such that sheath 26 may be placed over both stent 28 and balloon 36.

FIG. 2 shows a representative illustration of the stent delivery assembly 40 removed entirely from the delivery catheter body with guidewire 24 covered by sheath 26. Stent 28 is preferably placed directly over guidewire body 24 and is covered by sheath 26. Sheath 26 may have a flush port 42 located near the proximal end of the sheath 26. Flush port 42 is preferably in fluid communication with the distal end of the assembly 40 so that a fluid, e.g., saline, may be passed through the assembly 40 prior to insertion into the vasculature for flushing out air or debris trapped between the sheath 26 and guidewire 24. Flush port 42 may also be used to deliver drugs or fluids within the vasculature as desired.

Because the guidewire body 24, rather than a catheter body, carries and delivers stent 28 through the vasculature, the stent 28 may be placed almost anywhere in the body accessible by a conventional guidewire. This may include, e.g., the tortuous intracranial vasculature as well as, e.g., the more accessible coronary vasculature. Furthermore, assembly 40, which may include the guidewire 24, sheath 26, and stent 28, may be introduced into a wide variety of conventional catheters. This portability of assembly 40 allows for flexibility in using the same type of assembly 40 in an array of conventional catheters depending upon the desired application and the region of the body to be accessed.

The sheath 26 may be made from various thermoplastics, e.g., PTFE, FEP, Tecoflex, etc., which may optionally be lined on the inner surface of the sheath or on the outer surface of the guidewire or on both with a hydrophilic material such as Tecoflex or some other plastic coating. Additionally, either surface may be coated with various combinations of different materials, depending upon the desired results. Sheath 26 is preferably made to have a wall thickness of about 0.001 in. thick, and optionally thicker, and may have an outer diameter ranging from about 0.0145 to 0.016 in., or greater. Sheath 26 may also be placed over guidewire body 24 having a diameter of about 0.038 in. When placed over guidewire body 24 and stent 28, it may be simply placed over to slide along wire 24 or it may also be heatshrinked over the wire 24 and stent 28 to conform closely to the assembly.

A more detailed view of the guidewire assembly is shown in the cross sectioned side view in FIG. 3. As seen, the distal end of guidewire body 24 is shown loaded within sheath lumen 60 of sheath 26 and this assembly is shown as being disposed within catheter lumen 62 of catheter body 12. As previously discussed, because stent 28 is placed upon a guidewire body rather than a catheter body, the assembly may be introduced into any part of the body which is accessible by a conventional guidewire but which is not normally accessible for stenting treatments.

The guidewire body 24 may be made of a conventional guidewire and it may also be formed from a hypotube having an initial diameter ranging from 0.007 to 0.014 in. The hypotube or guidewire may be made from a variety of materials such as superelastic metals, e.g., Nitinol, or it may be made from metals such as stainless steel. During manufacture, a proximal uniform section 50 of the hypotube may be made to have a length of between about 39 to 87 in. (100 to 220 cm), preferably between about 63 to 71 in. (160 to 180 cm), having the initial diameter of 0.007 to 0.022 in., preferably 0.008 in. The hypotube may be further melted or ground down into a tapered section 52, depending upon the type of material used, which is distal to the proximal uniform section 50. Tapered section 52 may have a length of about 4 in. (10 cm) to reduce the diameter down to about 0.002 to 0.003 in. The hypotube may be further formed to have a distal uniform section 54 of about 2 in. (5 cm) in length over which the stent 28 is preferably placed. Radio-opaque marker bands may optionally be placed either distally 30 or proximally 32 of stent 28 to visually aid in the placement of the stent 28, as is well known in the art. Alternatively, distal and proximal marker bands 30, 32 may be eliminated altogether. Marker bands 30, 32 may be used as blocks or stops for maintaining the stent in its position along guidewire body 24. Alternatively, if bands 30, 32 are omitted from the device, stops or blocks may be formed integrally into the guidewire body 24 or they may be separately formed from material similar to that of guidewire body 24 and attached thereto.

Distal end 56 may be further tapered beyond distal uniform section 54 to end in distal tip 58, which is preferably rounded to aid in guidewire 24 advancement. A coil, preferably made from a radio-opaque material such as platinum, may be placed over a portion of distal end 56. Alternatively, a radio-opaque material, e.g., doped plastics such as bismuth or tungsten, may be melted down or placed over a portion of distal end 56 to aid in visualization. Stent 28 is preferably made to be self expanding from a constrained first configuration, as when placed upon guidewire 24 for delivery, to a larger expanded second configuration as when deployed within the vasculature. Stent 28 may be constrained by sheath 26 to a diameter of, e.g., 0.014 in., while being delivered to a treatment site within the body, but when sheath 26 is retracted proximally, stent 28 preferably self expands to a preconfigured diameter of, e.g., about 0.060 in. (1.5 mm), and up to a diameter of about 0.315 in. (8 mm). Various materials may be used to construct stent 28 such as platinum, Nitinol, other shape memory alloys, or other self expanding materials. Sheath 26 may also have drainage ports or purge holes 64 formed into the wall near the area covering stent 28. There may be a single hole or multiple holes, e.g., three holes, formed into sheath 26. Purge holes 64 allow for fluids, e.g., saline, to readily escape from inbetween sheath 26 and guidewire 24 when purging the instrument, e.g., to remove trapped air or debris.

FIG. 4 shows a cross sectioned side view of another variation 70 of the stent delivery assembly. As shown, guidewire variation 70 is shown as being surrounded by sheath 26 and the sheath-guidewire assembly is shown as being placed within catheter lumen 62 prior to delivery of the stent. In this variation, the guidewire may have a uniform section 72 like that described in FIG. 3 above. However, there is also a stepped section 74 defined in the guidewire outer diameter near the distal end of the guidewire. Within this section 74, the stepped outer diameter is less than the uniform diameter defined by the guidewire uniform section 72. It is over this stepped section 74 that stent 84 may be placed along with optional distal and/or proximal marker bands 80, 82, respectively, such that sheath 26 remains flush over this section. Maintaining a flush outer diameter may facilitate delivery of the stent-guidewire assembly not only through catheter body 12 but within the vasculature. The guidewire may be farther formed into tapered section 76 distally of stepped section 74. And the guidewire may be finally formed into a distal tip 78 over which coil 86 may be optionally placed. Coil 86 may optionally be covered by a covering 88, e.g., a polymer or other plastic material, placed or heatshrinked over the coil 86 and distal tip 78 to provide a smooth section.

FIG. 5 shows a cross sectioned side view of yet another variation of the stent delivery assembly having an expandable balloon section. As shown, much of the guidewire is similar to variations described above but with the addition of an expandable balloon 36 which may be inflated to an expanded balloon 36'. The variation shown may have a uniform section 90 which similarly tapers down 92 into a distal uniform section 94, over which stent 28 may be placed. Although balloon 36 may be placed proximally of stent 94, it is preferably located distally of stent 94, as shown. When deflated, retractable sheath 26 may also be placed over balloon 36 to provide a uniform profile. To accommodate the inflation and deflation of balloon 36, a small inflation lumen (not shown) may be defined within the body of the guidewire for the passage of fluids into and out of the balloon 36. A coil may also be optionally placed over distal end 96; alternatively, a radio-opaque material may be melted down or placed over distal end 96.

In operation, the stent delivery guidewire may be used with or without the catheter body to deliver the assembly intravascularly. It is preferable that a catheter be used to provide a pathway close to the treatment site. However, in tortuous pathways, such as intracranial vessels, the guidewire device may be used with the sheath alone if the catheter body presents too large a cross section for delivery purposes. FIGS. 6A to 6C show an example of the deployment of the guidewire assembly. Catheter body 12 may first be advanced within the lumen 102 of vessel 100 to a treatment location, e.g., aneurysm 104. Once catheter body 12 has reached a position near aneurysm 104, guidewire 24 may be advanced through and out of catheter 12 with sheath 26 covering stent 28, as seen in FIG. 6A. As guidewire 24 is advanced, stent 28 located on guidewire 24 may be positioned via radio-opaque marker bands 30, 32 to the desired location, such as over the neck 106 of aneurysm 104. Once guidewire 24 and stent 28 have been properly positioned, sheath 26 may be retracted proximally to expose stent 28 to the vascular environment, as shown in FIG. 6B.

Stent 28, as shown in FIG. 6C, may be left to radially self expand into gentle contact with the walls of vessel 100 to occlude the neck 106 of aneurysm 104 (as is well known in the art). Stent 28 may also be configured to expand upon the application of an electric current actuated from a location external of the patient. The current may be delivered to stent 28 via an electrical connection or line (not shown) disposed within the body of guidewire 24. Once the stent 28 has been released from the guidewire body 24 and expanded into contact with vessel 100, guidewire 24 and sheath 26 may be withdrawn into catheter body 12 and removed entirely from catheter 12 or the catheter 12 itself may then be removed entirely from the body of the patient. If guidewire 24 and sheath 26 are removed only, catheter 12 may be left in position within vessel 100 to allow for the insertion of additional tools or the application of drugs near the treatment site.

Treatment may also be accomplished with the guidewire variation having an expandable balloon section. FIG. 7A shows vessel 110 which is stenosed with an obstruction 112. Once catheter body 12 has been positioned within vessel 110, guidewire body 34 may be advanced out of catheter 12 while still covered by sheath 26. Balloon 36 may then be positioned adjacent to the obstruction 112 optionally guided by marker bands 30, 32. Once positioned, balloon 36 may be expanded to balloon 36', as shown in FIG. 7B, to open the stenosed vessel. After the obstruction 112 has been opened, balloon 36 may be deflated and the guidewire body 34 may be advanced distally to position sheath 28 adjacent to obstruction 112. Sheath 26 may then be retracted to expose stent 28 to expand, as described above, into contact against obstruction 112 and vessel 110. FIG. 7C shows the placement of guidewire 34 and expanding stent 28 over obstruction 112.

The applications of the guidewire assembly and methods of use discussed above are not limited to the deployment and use within the vascular system but may include any number of further treatment applications. Other treatment sites may include areas or regions of the body such as organ bodies. Modification of the above-described assemblies and methods for carrying out the invention, and variations of aspects of the invention that are obvious to those of skill in the art are intended to be within the scope of the claims.

What is claimed is:

1. A method for treating an aneurysm located within an intracranial vessel of a patient comprising:
   providing a radially self-expanding tubular prosthesis having a body defined by a cylindrical wall, the cylindrical wall having no circumferential free ends, at least a portion of the cylindrical wall having a plurality of through passages, the radially self-expanding tubular prosthesis having an unexpanded and expanded configuration, said unexpanded configuration having first inner and outer diameters and said expanded configuration having second inner and outer diameters greater than the first inner and outer diameters, respectively;
   providing an elongated metallic wire, said elongated metallic wire being devoid of an internal through lumen that extends between the proximal and distal ends and having a stop in a fixed position, said stop having a diameter greater than the unexpanded first inner diameter of the proximal end of the radially self-expanding tubular prosthesis, the radially self-expanding tubular prosthesis coaxially positioned in its unexpanded configuration on a distal segment of the elongated metallic wire and distal to said stop and further being fully releasable from the elongated metallic wire for placement across a neck of the aneurysm;
   providing an elongated sheath, said elongated sheath being slidable between a first position covering and radially constraining the radially self-expanding tubular prosthesis and a second position in which all of the radially self-expanding tubular prosthesis is uncovered, the radially self-expanding tubular prosthesis radially constrained on the distal segment of the elongated metallic wire;
   delivering the radially self-expanding tubular prosthesis and the elongated sheath to the aneurysm, the radially self-expanding tubular prosthesis carried by the elongated metallic wire so that the portion of the cylindrical wall having the plurality of through passages is positioned across the neck of the aneurysm; and
   sliding the elongated sheath from the first position to the second position to fully release the radially self-expanding tubular prosthesis from the elongated metallic wire so that the radially self-expanding tubular prosthesis is placed across the neck of the aneurysm in the expanded configuration, the elongated sheath at least partially constraining the radially self-expanding tubular prosthesis on the distal segment of the elongated metallic wire until the elongated sheath attains the second position.

2. A method for treating an aneurysm located within an intracranial vessel of a patient comprising:
   providing a radially self-expanding tubular prosthesis having a body defined by a cylindrical wall, the cylindrical wall having no circumferential free ends, at least a portion of the cylindrical wall having a plurality of through passages, the radially self-expanding tubular prosthesis having an unexpanded and expanded configuration, said unexpanded configuration having first inner and outer diameters and said expanded configuration having second inner and outer diameters greater than the first inner and outer diameters, respectively;
   providing an elongated metallic wire, said elongated metallic wire being devoid of an internal through lumen that extends between the proximal and distal ends and having a block in a fixed position, said block having a diameter greater than the unexpanded first inner diameter of the proximal end of the radially self-expanding tubular prosthesis, the radially self-expanding tubular prosthesis coaxially positioned in its unexpanded configuration on a distal segment of the elongated metallic wire and distal to said block and further being fully releasable from the elongated metallic wire for placement across a neck of the aneurysm;
   providing an elongated sheath, said elongated sheath being slidable between a first position covering and radially constraining the radially self-expanding tubular prosthesis and a second position in which all of the radially self-expanding tubular prosthesis is uncovered, the radially self-expanding tubular prosthesis radially constrained on the distal segment of the elongated metallic wire;
   delivering the elongated sheath and the radially self-expanding tubular prosthesis to the aneurysm, the radially self-expanding tubular prosthesis carried by the elongated metallic wire so that the portion of the cylindrical wall having the plurality of through passages is positioned across the neck of the aneurysm; and
   sliding the elongated sheath from the first position to the second position to fully release the radially self-expanding tubular prosthesis from the elongated metallic wire so that the radially self-expanding tubular prosthesis is placed across the neck of the aneurysm in the expanded configuration, the elongated sheath at least partially constraining the radially self-expanding tubular prosthesis on the distal segment of the elongated metallic wire until the elongated sheath attains the second position.

* * * * *